(12) United States Patent
Coulston et al.

(10) Patent No.: US 10,626,119 B2
(45) Date of Patent: Apr. 21, 2020

(54) PROCESS FOR THE PREPARATION OF CUCURBITURIL AND/OR ONE OR MORE DERIVATIVES THEREOF

(71) Applicant: AQDOT LIMITED, Cambridge, Cambridgeshire (GB)

(72) Inventors: Roger Coulston, Cambridge (GB); David Diec, Haverhill (GB); Guilherme Nogueira, Cambridge (GB); Johannes Gerardus De Rooij, Ermelo (NL)

(73) Assignee: AQDOT LIMITED, Cambridgeshire (GB)

( * ) Notice: Subject to any disclaimer, the term of this patent is extended or adjusted under 35 U.S.C. 154(b) by 0 days.

(21) Appl. No.: 16/383,806

(22) Filed: Apr. 15, 2019

(65) Prior Publication Data

US 2019/0241579 A1    Aug. 8, 2019

Related U.S. Application Data

(60) Division of application No. 15/967,006, filed on Apr. 30, 2018, now Pat. No. 10,308,657, which is a continuation of application No. PCT/GB2017/053776, filed on Dec. 18, 2017.

(30) Foreign Application Priority Data

Dec. 22, 2016  (GB) .................................. 1621948.7
Jul. 5, 2017   (GB) .................................. 1710811.9

(51) Int. Cl.
    *C07D 487/22* (2006.01)
(52) U.S. Cl.
    CPC ................. *C07D 487/22* (2013.01)

(58) Field of Classification Search
    CPC .................................................. C07D 487/22
    See application file for complete search history.

(56) References Cited

U.S. PATENT DOCUMENTS 6,793,839 B1 *  9/2004  Day .................... C07D 487/04
                                                            252/1
2010/0001215 A1   1/2010  Suzuki et al.
2013/0012721 A1   1/2013  Scherman et al.
2015/0297772 A1  10/2015  Kim et al.

FOREIGN PATENT DOCUMENTS

| WO | 00/68232 A1    | 11/2000 |
| WO | 2005/026168 A1 | 3/2005  |
| WO | 2005/090351 A1 | 9/2005  |
| WO | 2007/014214 A2 | 2/2007  |
| WO | 2011/077099 A2 | 6/2011  |

OTHER PUBLICATIONS

Mar. 31, 2017 Combined Search and Examination Report issued in British Patent Application No. 1621948.7.
Mar. 22, 2018 International Search Report issued in International Patent Application No. PCT/GB2017/053776.
Mar. 22, 2018 Written Opinion issued in International Patent Application No. PCT/GB2017/053776.

* cited by examiner

*Primary Examiner* — Erich A Leeser
(74) *Attorney, Agent, or Firm* — Oliff PLC

(57) ABSTRACT

This invention relates to a process of manufacturing cucurbituril and/or one or more derivatives thereof with low formaldehyde content and to the use of said cucurbituril and/or one or more derivatives thereof, in particular in consumer and industrial products, and in industrial processes.

12 Claims, 2 Drawing Sheets

PROCESS FOR THE PREPARATION OF CUCURBITURIL AND/OR ONE OR MORE DERIVATIVES THEREOF

This is a Divisional of U.S. application Ser. No. 15/967,006 filed Apr. 30, 2018, which is a Continuation of Application No. PCT/GB2017/053776 filed Dec. 18, 2017, which claims the benefit of British Application No. 1621948.7 filed Dec. 22, 2016 and British Application No. 1710811.9 filed Jul. 5, 2017. The disclosures of the prior applications is hereby incorporated by reference herein in their entireties.

FIELD OF THE INVENTION

This invention relates to cucurbituril and/or one or more derivatives thereof with low formaldehyde content, to a process of manufacturing said cucurbituril and/or one or more derivatives thereof and to the use of said cucurbituril and/or one or more derivatives thereof, in particular in consumer and industrial products, and in industrial processes.

BACKGROUND OF THE INVENTION

Cucurbiturils are known to bind a number of substances to form host-guest compounds and, for this reason, have high application potential in a number of applications.

According to the state of the art, the production of cucurbiturils is a chemical process, involving the polycondensation of glycoluril and formaldehyde under strongly acidic aqueous conditions at high temperatures. For example 9 M sulphuric acid or 5 M to 9 M hydrochloric acid is used as the reaction medium and the reaction temperature is higher than 75° C., usually between 75 and 90° C. The reaction time is typically in the order of 24 hours. Such a process is also described in U.S. Pat. No. 6,793,839.

A principal disadvantage of this process is the presence of unreacted formaldehyde in the product.

The regulatory constraints on formaldehyde are continuously increasing owing to the carcinogenic potential of this substance. Decreasing the level of residual formaldehyde in consumer products is therefore a recognised necessity. For example, natural formaldehyde levels as low as those measured in plant material such as fruits and vegetables (6 to 35 ppm) are highly desirable (EFSA Journal 2014; 12(2):3550).

Therefore, a process leading to the formation of cucurbiturils and/or one or more derivatives thereof with low residual formaldehyde levels, is highly desirable.

SUMMARY OF THE INVENTION

In a first aspect of the present invention, there is provided curcubituril and/or one or more derivatives thereof comprising less than 300 ppm formaldehyde, that is to say, provided is cucurbituril and/or one or more derivatives thereof with a residual formaldehyde level of less than 300 ppm. The cucurbituril and/or one or more derivatives thereof may comprise less than 200 ppm, less than 100 ppm, less than 50 ppm formaldehyde. Preferably, the cucurbituril and/or one or more derivatives thereof comprises less than 25 ppm formaldehyde. More preferably, the cucurbituril and/or one or more derivatives thereof comprises less than 10 ppm formaldehyde. Low levels of residual formaldehyde are advantageous for applications in pharmaceutical, personal care, household, industrial and consumer products.

In a second aspect of the invention, there is provided a process for the preparation of cucurbituril and/or one or more derivatives thereof comprising mixing glycoluril or a derivative thereof with a methylene bridging agent, in the presence of an acid, and in the absence of any formaldehyde or formaldehyde precursor. In particular, the methylene bridging agent is a dialkoxymethane reagent.

The glycoluril is selected from the group consisting of unsubstituted glycoluril, alkoxy methylated glycoluril, other derivatives thereof, and a mixture thereof.

In a third aspect of the invention, there is provided a process for the preparation of cucurbituril and/or one or more derivatives thereof comprising mixing a fully alkoxy methylated glycoluril with unsubstituted glycoluril in the presence of an acid, and in the absence of any formaldehyde or a formaldehyde precursor.

In one embodiment, the fully alkoxy methylated glycoluril is tetramethoxymethylglycoluril.

In one embodiment, the acid used in the second and third aspects is a mineral acid or an organic acid. The acid may be selected from sulfuric acid, nitric acid, hydrochloric acid, hydrobromic acid, hydroiodic acid, phosphoric acid, toluenesulfonic acid and methanesulfonic acid.

In one embodiment, the acid is methanesulfonic acid.

In a fourth aspect of the invention, there is provided cucurbituril and/or one or more derivatives thereof obtained or obtainable by the process described in the second or third aspects of the invention.

In a fifth aspect of the invention, there is provided a composition comprising cucurbituril and/or one or more derivatives thereof comprising less than 300 ppm formaldehyde and a suitable carrier.

In a sixth aspect of the invention, there is provided use of cucurbituril and/or one or more derivatives thereof described in the first or fourth aspect in consumer or industrial products.

DETAILED DESCRIPTION OF THE INVENTION

The present inventors have found a process for preparing cucurbiturils and/or one or more derivatives thereof without adding any formaldehyde or formaldehyde precursor as starting reagent. The cucurbiturils and/or one or more derivatives thereof obtained by this process are particularly clean and free of residual formaldehyde. Advantageously, the formaldehyde free cucurbituril and/or one or more derivatives thereof is obtained without the need for the onerous purification steps often required with the prior art methods.

Cucurbituril

The present invention provides formaldehyde free cucurbituril and/or one or more derivatives thereof.

Cucurbituril is a member of the cavitand family, and the general cucurbituril structure is based on the cyclic arrangement of glycoluril subunits linked by methylene bridges.

Figure 1:
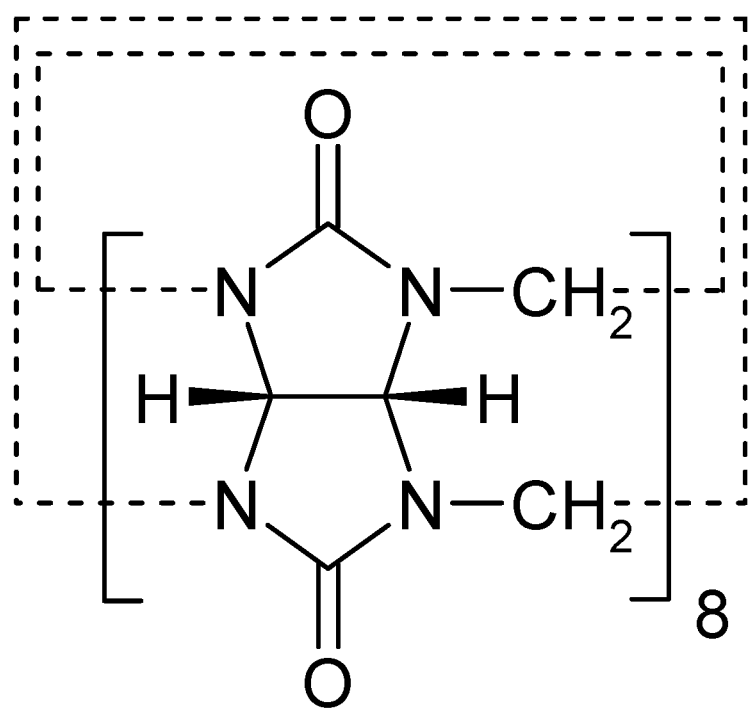
FIG. 1 is a schematic representation of cucurbit[8]uril (CB[8]; CAS 259886-51-6), which is a barrel shaped container molecule that has eight repeat glycoluril units.

For example, cucurbit[8]uril (CB[8]; CAS 259886-51-6) is a barrel shaped container molecule which has eight repeat glycoluril units and an internal cavity volume of 479 $Å^3$ (see the structure illustrated in FIG. 1).

In one embodiment, the cucurbituril is a CB[5], CB[6], CB[7], CB[8], CB[9], CB[10], CB[11], CB[12], CB[13] or CB[14] compound.

In one embodiment, the cucurbituril is a CB[5], CB[6], CB[7], CB[8], CB[9], CB[10], CB[11] or CB[12] compound.

In one embodiment, the cucurbituril is a CB[5], CB[6], CB[7], or CB[8] compound.

In one embodiment, the cucurbituril is a CB[6] compound.

In one embodiment, the cucurbituril is a CB[7] compound.

In one embodiment, the cucurbituril is a CB[8] compound.

The cucurbituril of the invention may include a single analogue of cucurbituril, or may alternatively include two or more different sized cucurbiturils selected from the group consisting of CB[5], CB[6], CB[7], CB[8], CB[9], CB[10], CB[11], CB[12], CB[13] and CB[14]. A mixture of two or more different cucurbiturils is defined as CB[n].

In one embodiment, the cucurbituril is a CB[n] mixture.

When the cucurbituril of the invention comprises at least two different cucurbiturils selected from CB[5], CB[6], CB[7] and CB[8]), the total concentration of the CB[5], CB[6], CB[7] and/or CB[8] may be greater than 75% by weight, more particularly greater than about 90% by weight, more particularly greater than about 99% by weight of the total weight of cucurbituril. The remaining components of the cucurbituril may contain CB[4], CB[9] and/or higher cucurbiturils (i.e. CB[10]-CB[20]), either as a single sized cucurbituril or as a mixture of these sizes.

The % weights of cucurbiturils described above are based on the total weight of cucurbituril (of all sizes).

Figure 2:
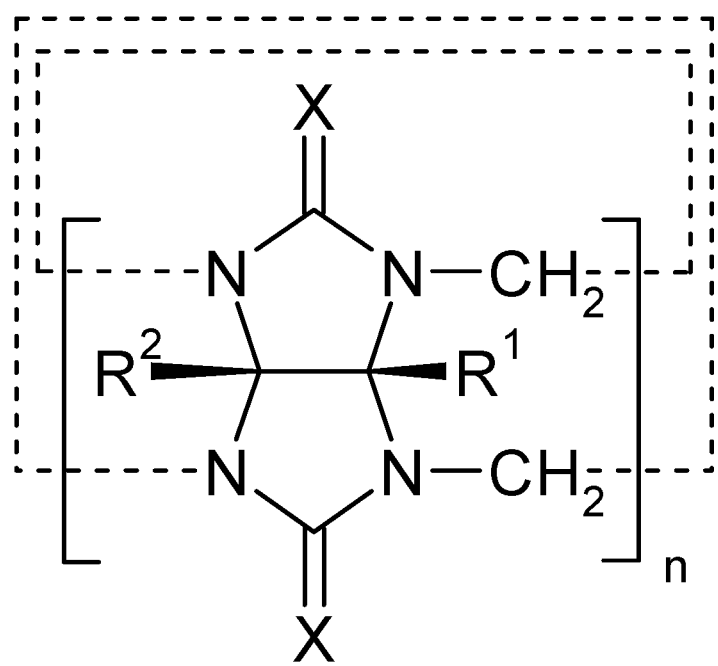
FIG. 2 is a schematic representation of a substituted cucurbituril compound.

Cucurbituril derivatives are provided and find use in the compositions and applications described herein. A derivative of a cucurbituril is a structure having one, two, three, four or more substituted glycoluril units. A substituted cucurbituril compound may be represented by the structure illustrated in FIG. 2, wherein:
n is an integer between 4 and 20;
and for each glycoluril unit:
each X is O, S or $NR^3$, and
—$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl group, $C_{6-20}$carboaryl group, and $C_{5-20}$heteroaryl group, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$carbocyclic ring together with the uracil frame.

In one embodiment, one of the glycoluril units is a substituted glycoluril unit. Thus, —$R^1$ and —$R^2$ are each independently —H for n−1 of the glycoluril units.

In one embodiment, n is 5, 6, 7, 8, 9, 10, 11 or 12.

In one embodiment, n is 5, 6, 7 or 8.

In one embodiment, each X is O.

In one embodiment, each X is S.

In one embodiment, $R^1$ and $R^2$ are each independently H.

In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl group, most preferably $C_{1-6}$alkyl group. The $C_{1-20}$alkyl group may be linear and/or saturated. Each group —$R^3$ may be independently unsubstituted or substituted. Preferred substituents are selected from: —$R^4$, —OH, —$OR^4$, —SH, —$SR^4$, —COOH, —$COOR^4$, —$NH_2$, —$NHR^4$ and —$N(R^4)_2$, wherein —$R^4$ is selected from $C_{1-20}$alkyl group, $C_{6-20}$carboaryl group, and $C_{5-20}$heteroaryl group. The substituents may be independently selected from —COOH and —$COOR^4$.

In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$OR^4$, —$NHR^4$ or —$N(R^4)_2$. Each —$R^4$ is $C_{1-6}$alkyl and is itself preferably substituted.

The cucurbiturils of the invention may be in the native form or they may be modified as described above in order to improve solubility or suspendability, and more generally their formulation and handling.

The cucurbituril and/or one or more derivatives thereof of the present invention are characterised by low levels of residual formaldehyde.

In one embodiment, the cucurbituril and/or one or more derivatives thereof comprises less than 300 ppm formaldehyde, that is to say, the weight ratio of formaldehyde to cucurbituril and/or one or more derivatives thereof is 300:1 000 000 or 3:10 000, more particularly, less than 200 ppm formaldehyde, even more particularly less than 100 ppm formaldehyde, for example less than 50 ppm formaldehyde, preferably less than 25 ppm formaldehyde.

In one embodiment, the cucurbituril and/or one or more derivatives thereof is free of formaldehyde. As used herein, the term "free of formaldehyde" or "formaldehyde free" is intended to mean cucurbituril with levels of formaldehyde which are equivalent to those found in nature, i.e. with less than 25 ppm of formaldehyde, more particularly less than 10 ppm of formaldehyde.

Suitable methods for measuring the level of formaldehyde in cucurbituril and/or one or more derivatives thereof will be known to those skilled in the art. The level of residual formaldehyde in samples can be determined using HPLC with fluorescence detection. Post column derivatisation of free formaldehyde is done using Nash reagent in a compartment of the HPLC system by automatic pump. The derivatisation is done inline, therefore all portions eluting from the column will react. Fluorescence is then used to measure the quantity of formaldehyde in the sample.

Process

The cucurbituril and/or one or more derivatives thereof with low formaldehyde content may be prepared by mixing unsubstituted glycoluril and/or a derivative thereof with a methylene bridging agent, in the presence of an acid.

The terms "methylene bridging agent" and "reagent" are used interchangeably throughout.

The reaction of unsubstituted glycoluril and/or a derivative thereof and the reagent is required to take place in the presence of an acid. The acid acts to catalyse the reaction(s) taking place. Without the acid, the unsubstituted glycoluril and/or a derivative thereof and the reagent will not react.

Suitable acids for use in the processes described herein include strong acids. Examples of strong acids include mineral acids and organic acids, such as sulfuric acid, hydrochloric acid, hydrobromic acid, hydroiodic acid, phosphoric acid, toluenesulphonic acid, and alkanesulphonic acid. However in principle, any acid can be used.

In particular the acid used is an alkanesulphonic acid. Examples of alkanesulphonic acids include methanesulphonic acid, ethanesulphonic acid, n-propanesulphonic acid, isopropanesulphonic acid, n-butanesulphonic acid, isobutanesulphonic acid, sec-butanesulphonic acid, tert-butanesulphonic acid, and mixtures thereof.

In one embodiment, the acid is methanesulphonic acid.

In one embodiment, the unsubstituted glycoluril and/or a derivative thereof and the acid are mixed together simultaneously. The acid may be present in excess which allows the unsubstituted glycoluril and/or a derivative thereof to dissolve in the acid. The reagent is then added portion-wise or drop-wise to the unsubstituted glycoluril and/or a derivative thereof and acid mixture.

Alternative methods include simultaneous addition of the unsubstituted glycoluril and/or a derivative thereof, the acid and reagent. Another method involves the sequential addition of the unsubstituted glycoluril and/or a derivative thereof, the acid and the reagent. For example, the reagent may be added to the acid followed by the unsubstituted glycoluril and/or a derivative thereof.

The acid may be a heterogeneous acid where the phase of the acid is different to that of the reagents. Alternatively, the acid may be a homogeneous acid where the acid and the reagents are in the same phase.

Once all the components are added, the reaction mixture is then heated to a temperature of between 40° C. and 200° C. Alternatively, the unsubstituted glycoluril and/or a derivative thereof and the acid may be mixed in a heated reaction vessel before addition of the reagent. The heated reaction vessel may also be at a temperature of 40° C. to 200° C.

In one embodiment, the process is carried out at a temperature of at least 40° C., more particularly at least 80° C., still more particularly at least 90° C. For example, the process may be carried out at a temperature from about 40° C. to about 200° C., in particular, from about 70° C. to about 110° C., more particularly, from about 75° C. to 100° C. For example, the process may be carried out at a temperature of about 75° C., about 85° C. or about 100° C.

The process may be reacted for up to 24 hours. More particularly, the process is reacted for up to 20 hours, for example up to 18 hours. However, shorter reaction times are possible and in certain instances, the process is reacted for up to 1 hour, for example up to 45 minutes or up to 30 minutes.

After prolonged heating of the reaction mixture, the mixture may be cooled, for example, to room temperature.

Finally, the processes described herein may further comprise a purification step. In one embodiment the purification step is a washing step. Alternative purification steps include recrystallization. Washing of the reaction mixture can be done with any suitable solvent. Such solvents will be well known to the skilled person and examples include acetone and methanol. Washing of the reaction mixture is often required in order to remove any remaining reagent and acid. However, as a result of the cleaner reaction, the washing and drying steps in the processes of the present invention are far less onerous compared to the prior art processes.

Formaldehyde scavengers, such as β-dicarbonyl compounds, amides, imines, acetal formers, sulfur containing compounds, activated carbon, ammonium, organic amines, an oxidizing agent or mixtures thereof, are often used as a purification step in prior art methods. Such methods are disclosed in US 2007/0138671, herein incorporated by reference. However, again as the result of the cleaner reaction, the processes described herein minimise, if not eliminate, the need for scavengers in the end product.

Depending on the glycoluril derivative used, there are instances where the reaction of unsubstituted glycoluril and/or a derivative thereof in the presence of an acid can be performed in the absence of a methylene bridging reagent. For example, when the starting glycolurils are a mixture of fully alkoxy methylated glycoluril and unsubstituted glycoluril, no external methylene bridging agent (e.g. dialkoxy methane reagent) is needed.

Therefore, in a further aspect of the invention, there is provided a process for the preparation of cucurbituril comprising reacting a fully alkoxy methylated glycoluril with unsubstituted glycoluril in the presence of an acid, as described above, but in the absence of a methylene bridging agent.

In one embodiment, the fully alkoxy methylated glycoluril is 1,3,4,6-tetrakis(methoxymethyl)glycoluril (CAS No. 17464-88-9), which may also be referred to throughout as tetramethoxymethylglycoluril (TMMG).

Importantly, the processes described herein are carried out in the absence of any formaldehyde, or any formaldehyde producing precursor. The term "formaldehyde" refers to a compound with formula $CH_2O$ and includes formalin which is an aqueous solution of formaldehyde. The terms "formaldehyde producing precursor" or "formaldehyde precursor" are used interchangeably throughout and refer to polymers and oligomers of formaldehyde which exist in equilibrium with formaldehyde in water. Examples of formaldehyde precursors include paraformaldehyde (a linear polymer of formaldehyde) and trioxane (a cyclic trimer of formaldehyde), both of which have similar chemical properties to formaldehyde and are often used interchangeably. Other formaldehyde precursors will be known to the skilled person.

Advantageously, the methylene bridging agents of the present invention, for example compounds of formula (IV), do not exist in equilibrium with formaldehyde in water.

Glycoluril

Glycolurils are the monomer units that make up cucurbituril. The glycolurils are selected from the group consisting of unsubstituted glycoluril, alkoxy-methylated glycoluril, other derivatives thereof, and a mixture thereof.

In one embodiment, the glycoluril is represented by formula (I):

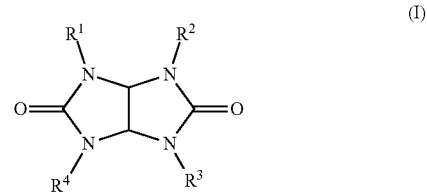

(I)

wherein $R^1$, $R^2$, $R^3$ and $R^4$ each independently represent hydrogen or $-CH_2-O-C_1-C_4$ alkyl.

When at least one of $R^1$, $R^2$, $R^3$ and $R^4$ is $-CH_2-O-C_1-C_4$ alkyl group, the glycoluril may be referred to as an alkoxy-methylated glycoluril. When $R^1$, $R^2$, $R^3$ and $R^4$ are each hydrogen, the glycoluril may be referred to as unsubstituted glycoluril.

The $-CH_2-O-C_1-C_4$ alkyl group is preferably unsubstituted.

For a mono-alkoxy methylated glycoluril, one of the $R^1$, $R^2$, $R^3$ and $R^4$ groups represents $-CH_2-O-C_1-C_4$ alkyl group whilst the remaining groups represent hydrogen. For a di-alkoxy methylated glycoluril, two of the $R^1$, $R^2$, $R^3$ and $R^4$ groups each independently represent —$CH_2$—O—$C_1$-$C_4$ alkyl group whilst the remaining groups represent hydrogen. For a tri-alkoxy methylated glycoluril, three of the $R^1$, $R^2$, $R^3$ and $R^4$ groups each independently represent —$CH_2$—O—$C_1$-$C_4$ alkyl group whilst the remaining group represents hydrogen. Finally for a tetra-alkoxy methylated glycoluril, four of the $R^1$, $R^2$, $R^3$ and $R^4$ groups each independently represent —$CH_2$—O—$C_1$-$C_4$ alkyl group.

In one embodiment, the alkoxy methylated glycoluril is selected from mono-alkoxy methylated, di-alkoxy methylated, tri-alkoxy methylated and tetra-alkoxy methylated glycoluril or a mixture thereof.

In one embodiment, the glycoluril is monomethoxymethylglycoluril, dimethoxymethylglycoluril, trimethoxymethylglycoluril, tetramethoxymethyiglycoluril, or a mixture thereof.

In another embodiment, $R^1$, $R^2$, $R^3$ and $R^4$ each represent hydrogen and the glycoluril is therefore unsubstituted glycoluril and is represented by formula (II):

(II)

The unsubstituted or monomethoxy methylated, dimethoxymethylated or trimethoxymethylated glycoluril is reacted with a methylene bridging reagent under the conditions described hereinabove.

In one embodiment, the glycoluril is tetramethoxymethylglycoluril (TMMG), which has the structure of formula (III):

(III)

When the glycoluril is TMMG, the reaction of TMMG with unsubstituted glycoluril in the presence of acid can be performed in the absence of a methylene bridging reagent, as described above.

Reagent

Certain processes described herein involve the reaction of a reagent with glycolurils. The reagent must be a compound capable of forming methylene bridges between the glycoluril units. The reagent cannot be formaldehyde, or a formaldehyde precursor, for example paraformaldehyde or trioxane.

One class of suitable reagents are compounds with the formula (IV):

(IV)

wherein each X is independently selected from an electronegative atom;
$R_1$ and $R_2$ are each independently selected from hydrogen, an unsubstituted or substituted straight chain, branched or cyclic, saturated or unsaturated hydrocarbon radical; and
R represents hydrogen.

In one embodiment, each X is selected from oxygen, nitrogen, sulphur and phosphorus.

In one embodiment, the straight chain, branched or cyclic saturated or unsaturated hydrocarbon radical is substituted with halogen, hydroxyl, cyano, oxo, nitro or $C_1$-$C_3$ alkoxy.

Examples of compounds of formula (IV) include dimethoxymethane, diethoxymethane, dipropoxymethane, dibutoxymethane, 1,3-dioxacyclopentane, methylidinoglycerol, 2,4-dithiapentane, bis(phenylthio)methane, bis(dimethylphosphino)methane, methylene diacetate and methanediol.

In one embodiment, the reagent is selected from dialkoxymethane, diethoxymethane and dipropoxymethane.

The dialkoxymethane may be selected from dimethoxymethane, diethoxymethane, dipropoxymethane (1-(propoxymethoxy)propane), diisopropoxymethane (2-(isopropoxymethoxy)propane), dibutoxymethane (1-(butoxymethoxy)butane), di(tert-butoxy)methane (2-methyl-2-{[(2-methyl-2-propanyl)oxy] methoxy}propane), and mixtures thereof.

In one embodiment, the reagent is dimethoxymethane.

Other suitable reagents include 1,3-cycloketals.

1,3-cycloketals include 1,3-dioxolane, 1,3-dioxane, glycerol formal, 1,3-dioxepane, 1,3-dioxopane, Poly(vinyl formal), and the like.

Other suitable reagents include alkoxymethyl alkane sulphonate, for example methoxymethane methane sulphonate, methoxymethyl benzenesulphonate, methoxymethyl p-toluene sulphonate, benzyloxymethyl methanesulphonate, and the like.

Compositions

In one aspect of the invention there is provided a composition comprising cucurbituril and/or one or more derivatives thereof with low levels of residual formaldehyde.

In another aspect, a composition is provided, the composition comprising cucurbituril and/or one or more derivatives thereof, the composition further comprising no more than 300, preferably no more than 150, more preferably no more than 50, most preferably no more than 10 ppm formaldehyde originating from the cucurbituril and/or one or more derivatives thereof, that is to say formaldehyde originating from the process of preparing the cucurbituril and/or one or more derivatives thereof. By way of a benchmark, apple comprises about 35 ppm formaldehyde.

A composition may be a liquid or a solid, such as powder, composition.

The composition may further comprise excipients such as preservatives, dyes, pigments, sequestrants, surfactants and antioxidants.

One advantage of a composition with low levels of residual formaldehyde originating from the process of preparation of cucurbituril and/or one or more derivatives thereof is that it provides more formulation space to include other excipients which also have residual formaldehyde without the overall level of formaldehyde in any finished composition being such as to be a drawback. Such a composition can be a consumer product.

The present case also provides a method of preparing a composition, the method comprising the step of mixing cucurbituril and/or one or more derivatives thereof with low levels of residual formaldehyde, as described herein, with one or more excipients, such as those used in consumer and industrial products, and such as those excipients discussed above.

In a further aspect of the invention there is provided a consumer or industrial product comprising the cucurbituril and/or one or more derivatives thereof of the present invention.

The consumer product of the invention may be a detergent, a cleansing composition, a shampoo, a softener, a softener sheet, a conditioner, a refresher, an air freshener, a deodorizing composition, a personal deodorant, a carrier for a catalyst, a drug delivery device, a medical device, an antiperspirant, a cosmetic product, a fine fragrance, a body mist, a candle, a hard surface cleaner, a cleansing wipe or mop, a soap, a styling gel, a humidity absorber, an air filtration device, a finishing product, a diaper or sanitary product, and the like.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of examples 5 to 8. Examples 1 to 4 are prior art methods.

Experimental and Results

The level of residual formaldehyde in the cucurbituril samples was determined by Intertek using HPLC with fluorescence detection and post column derivatization. The testing method followed EU Directive 82/434/EEC amendment 90/207/EEC.

Example 1 Synthesis of Cucurbit[n]Urils in Hydrochloric Acid Using Paraformaldehyde Unsubstituted glycoluril (20 g) and hydrochloric acid (37% w/v, 30 mL) were placed in a reaction flask and heated to 90° C. Paraformaldehyde (8.87 g) was added in portionwise and the reaction mixture was then heated to 100° C. (internal) for 18 hours. The reaction mixture was cooled and added to methanol (150 mL) to produce a beige powder which was analysed by $^1$H NMR.

Approximate Yields by $^1$H NMR (% of recovered product) cucurbit[5]uril 8%, cucurbit[6]uril 44%, cucurbit[7]uril 28%, cucurbit[8]uril 18%, cucurbit[9]uril 0%, cucurbit[10]uril 0% cucurbit[11]uril 0%.

Residual formaldehyde by HPLC method was 682 ppm.

Example 2 Synthesis of Cucurbit[n]Urils in Hydrochloric Acid Using Formalin

Unsubstituted glycoluril (20 g) and hydrochloric acid (37% w/v, 30 mL) were placed in a reaction flask and heated to 90° C. Formalin (40% v/v, 21 mL) was added dropwise and the reaction mixture heated to 100° C. (internal) for 18 hours. The reaction mixture was cooled and added to methanol (150 mL) to produce a yellow powder which was analysed by $^1$H NMR.

Approximate Yields by $^1$H NMR (% of recovered product) cucurbit[5]uril 8%, cucurbit[6]uril 38%, cucurbit[7]uril 38%, cucurbit[8]uril 11%, cucurbit[9]uril 0%, cucurbit[10]uril 0% cucurbit[11]uril 0%.

Residual formaldehyde by HPLC method was 567 ppm.

Example 3 Synthesis of Cucurbit[n]Urils in Methanesulphonic Acid (MSA) Using Paraformaldehyde Unsubstituted glycoluril (20 g) and methanesulphonic acid (neat, 82 mL) were placed in a reaction flask and heated to 90° C. Paraformaldehyde (8.45 g) was added in portionwise and the reaction mixture was then heated to 100° C. (internal) for 18 hours. The reaction mixture was cooled and added to methanol (410 ml) to produce a brown powder which was analysed by $^1$H NMR.

Approximate Yields by $^1$H NMR (% of recovered product) cucurbit[5]uril 0%, cucurbit[6]uril 63%, cucurbit[7]uril 35%, cucurbit[8]uril 0%, cucurbit[9]uril 0%, cucurbit[10]uril 0% cucurbit[11]uril 0%.

Residual formaldehyde by HPLC method was 1621 ppm.

Example 4 Synthesis of Cucurbit[n]Urils in Methanesulphonic Acid Using Formalin

Unsubstituted glycoluril (20 g) and methanesulphonic acid (neat, 82 mL) were placed in a reaction flask and heated to 90° C. Formalin (40%, 21 mL) was added in drop-wise and the reaction mixture was then heated to 100° C. (internal) for 18 hours. The reaction mixture was cooled and added to methanol (410 ml) to produce a dark beige powder which was analysed by $^1$H NMR.

Approximate Yields by $^1$H NMR (% of recovered product) cucurbit[5]uril 6%, cucurbit[6]uril 48%, cucurbit[7]uril 36%, cucurbit[8]uril 8%, cucurbit[9]uril 0%, cucurbit[10]uril 0%, cucurbit[11]uril 0%.

Residual formaldehyde by HPLC method was 820 ppm.

Example 5 Synthesis of Cucurbit[n]Urils in Methanesulphonic Acid Using Dimethoxymethene (Methylal)

Methanesulphonic acid (neat, 82 ml) was added to the reaction vessel. To this methylal (24.83 ml) was added to the reaction. Unsubstituted glycoluril (19.94 g) was added immediately afterwards in one portion and the reaction mixture was heated to 85° C. (internal) for 18 hours. The reaction mixture was added to methanol (250 ml) to produce a dark brown gummy paste which was analysed by $^1$H NMR.

Approximate Yields by ¹H NMR (% of recovered product) cuc urbit[5]uril 0%, cucurbit[6]uril 65%, cucurbit[7]uril 35%, cucurbit[8]uril 0%, cucurbit[9]uril 0%, cucurbit[10] uril 0%, cucurbit[11]uril 0%.

Residual formaldehyde by HPLC method was 24 ppm.

Example 6 Synthesis of Cucurbit[n]Urils in Methanesulphonic Acid Using Diethoxymethane (Ethylal)

Unsubstituted glycoluril (19.94 g) and methane sulphonic acid (neat, 82 mL) were placed in a reaction flask and heated to 80° C. Ethylal (35.21 mL) was added in drop-wise and the reaction mixture was then heated to 100° C. (internal temp) for 18 hours. The reaction mixture was cooled and added to acetone (410 ml) to produce a brown powder which was analysed by ¹H NMR.

Approximate Yields by ¹H NMR (% of recovered product) cucurbit[5]uril 8%, cucurbit[6]uril 42%, cucurbit[7]uril 43%, cucurbit[8]uril 7%, cucurbit[9]uril 0%, cucurbit[10] uril 0%, cucurbit[11]uril 0%.

Residual formaldehyde by HPLC method was 34 ppm.

Example 7 Synthesis of Cucurbit[n]Urils in Methanesulphonic Acid Using Dipropoxymethane (Propylal)

Unsubstituted glycoluril (19.94 g) and methane sulphonic acid (neat, 82 mL) were placed in a reaction flask and heated to 80° C. Propylal (45 mL) was added in drop-wise and the reaction mixture was then heated to 100° C. (internal temp) for 18 hours. The reaction mixture was cooled and added to acetone (410 ml) to produce a beige powder which was analysed by ¹H NMR.

Approximate Yields by ¹H NMR (% of recovered product) cucurbit[5]uril 0%, cucurbit[6]uril 58%, cucurbit[7]uril 42%, cucurbit[8]uril 0%, cucurbit[9]uril 0%, cucurbit[10] uril 0%, cucurbit[11]uril 0%.

Residual formaldehyde by HPLC method was 5 ppm.

Example 8 Synthesis of Cucurbit[n]Urils in Methanesulphonic Acid Using Tetramethoxymethylglycoluril (TMMG)

Unsubstituted glycoluril (19.94 g) and methane sulphonic acid (neat, 82 mL) were placed in a reaction flask and heated to 80° C. TMMG (44.66 g) was added in drop-wise and the reaction mixture was then heated to 100° C. (internal temp) for 18 hours. The reaction mixture was cooled and added to methanol (410 ml) to produce a beige powder which was analysed by ¹H NMR.

Approximate Yields by ¹H NMR (% of recovered product) cucurbit[5]uril 5%, cucurbit[6]uril 58%, cucurbit[7]uril 28%, cucurbit[8]uril 9%, cucurbit[9]uril 0%, cucurbit[10] uril 0%, cucurbit[11]uril 0%.

Residual formaldehyde by HPLC method was 293 ppm.

TABLE 1

Summary of Results

| Example | Residual Formaldehyde content (ppm) |
|---|---|
| 1 | 682 |
| 2 | 567 |
| 3 | 1621 |
| 4 | 820 |
| 5 | 24 |
| 6 | 34 |
| 7 | 5 |
| 8 | 293 |

The invention claimed is:

1. A process for the preparation of cucurbituril and/or one or more derivatives thereof comprising mixing glycoluril with a methylene bridging agent, in the presence of an acid and in the absence of any formaldehyde, or formaldehyde precursor, wherein the glycoluril is selected from the group consisting of unsubstituted glycoluril, alkoxy-methylated glycoluril, glycoluril derivatives, and mixtures thereof.

2. The process according to claim 1, wherein the glycoluril, the methylene bridging agent and the acid are mixed simultaneously, or are mixed sequentially.

3. The process according to claim 2, wherein the glycoluril is the alkoxy-methylated glycoluril, the alkoxy-methylated glycoluril being selected from the group consisting of a monoalkoxy-methylated glycoluril, a dialkoxy-methylated glycoluril, a trialkoxy-methylated glycoluril, and a mixture thereof.

4. The process according to claim 1, wherein the methylene bridging agent is a compound of formula (IV):

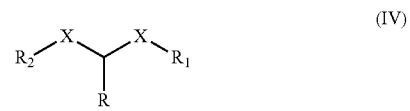

(IV)

wherein each X is independently selected from the group consisting of an electronegative atom, oxygen, nitrogen, sulphur and phosphorus;

$R_1$ and $R_2$ are each independently selected from hydrogen, an unsubstituted or substituted straight chain, branched or cyclic, saturated or unsaturated hydrocarbon radical; and R represents hydrogen.

5. The process according to claim 1, wherein the methylene bridging agent is one or more members selected from the group consisting of a dialkoxymethane reagent, dimethoxymethane, diethoxymethane, dipropoxymethane (1-(propoxymethoxy)propane), diisopropoxymethane (2-(iso-propoxymethoxy)propane), dibutoxymethane (1-(butoxymethoxy)butane), di(tert-butoxy)methane (2-methyl-2-{[(2-methyl-2-propanyl)oxy]methoxy}propane), and mixtures thereof.

6. The process according to claim 1, wherein the methylene bridging agent is one or more members selected from the group consisting of an alkoxymethyl alkanesulphonate, methoxymethane methane sulphonate, methoxymethyl benzenesulphonate, methoxymethyl p-toluene sulphonate, benzyloxymethyl methanesulphonate, and mixtures thereof.

7. The process according to claim 1, wherein the acid is a heterogeneous acid or a homogeneous acid, wherein when the acid is a heterogeneous acid, the heterogeneous acid is on a solid support such as an acidic resin.

8. The process according to claim 1, wherein the acid is selected from the group consisting of a mineral acid, an organic acid, sulfuric acid, nitric acid, hydrochloric acid, hydrobromic acid, hydroiodic acid, phosphoric acid, toluenesulphonic acid, and alkanesulphonic acid.

9. The process according to claim 1, wherein the acid is methanesulphonic acid.

10. The process according to claim 1, wherein the acid is provided in excess.

11. The process according to claim 1, wherein the process is carried out at a temperature greater than 40° C.

12. The process according to claim 1, wherein the glycoluril, the methylene bridging agent, if present, and the acid are reacted for up to 18 hours.

* * * * *